United States Patent [19]

Mukherjee et al.

[11] Patent Number: 5,744,363
[45] Date of Patent: Apr. 28, 1998

[54] METHOD FOR ESTABLISHING A TUMOR-CELL LINE BY PREPARING SINGLE-CELL SUSPENSION OF TUMOR CELLS FROM TUMOR BIOPSIES

[75] Inventors: Rama Mukherjee; Manu Jaggi, both of New Delhi, India

[73] Assignee: National Institute of Immunology, New Delhi, India

[21] Appl. No.: 764,571

[22] Filed: Dec. 13, 1996

Related U.S. Application Data

[63] Continuation-in-part of Ser. No. 727,679, Oct. 8, 1996.

[30] Foreign Application Priority Data

Aug. 16, 1996 [IN] India ................................ 1822/96
Oct. 31, 1996 [IN] India ................................ 2381/96

[51] Int. Cl.$^6$ ................................................ C12N 5/00
[52] U.S. Cl. .................... 435/378; 435/379; 435/383; 435/366; 435/353; 435/354
[58] Field of Search ............................ 435/378, 379, 435/383, 366, 353, 354

[56] References Cited

U.S. PATENT DOCUMENTS 5,273,963 12/1993 Moody ............................... 514/12
5,434,132 7/1995 Rozengurt ............................ 514/2

OTHER PUBLICATIONS

Jaggi et al., Journal of Basic & Applied Biomedicine, 3(4) : 27–35, 1995.
M. Jaggi et al., "Establishment of Tumorigeric Cell . . . " JBAB–ABS06(mj)12–95 3(4) : 27–35.
X. Fu et al., "A Metastatic Nude–Mouse . . . " Proc. Natl. Acad. Sci, USA, vol. 89, pp. 5645–5649 Jun. 1992.
B. Rae–Ventor et al., "Growth of Human Breast . . . " Cancer Research 40, 95–100 Jan. 1980 pp. 95–98.
P. Giovanella, et al. "Correlation Between Response . . . " Cancer. Oct. 1, 1983, 52 : 1146–1152.
R. Giavazzi et al "Metastatic Behavior . . . " Cancer Research 46, 1928–1933, Apr. 1986.
Peters, L.C. "Preparation of Immunotherapeutic . . . " Cancer Research 39: 1353–1360 (Apr. 1979).
E. Bombardieri, et al., "Somatostatin Receptor Imaging of Small Cell Lung Cancer . . . Scintigraphy," European Journal of Cancer, vol. 31A, No.2, pp.184–188, 1995.
J. Pinski et al., "Somatostatin Analogues and Bombesin/Gastrin . . . in vitro and in vivo," Peptide Analogues in Glioblastomas, vol. , pp.5895–5901, (1994).
P.A. Bunn, Jr., et al., "Effects of Neuropeptide Analogues on . . . Cancer Cell Lines," Cancer Research 54, pp.3602–3610, Jul. 1, 1994.
G. Lilling, et al., "Inhibition of Human Neuroblastoma . . . VIP Antagonist," Journal of Molecular Neuroscience, vol. 5, 1994/1995, pp. 231–239.

H. Reile, et al., "Characterization of High–Affinity Receptors For Bombesin/Gastrin Releasing . . . By Tumor Cells," The Prostate 25:29–38, (1994).
I. Virgolini, M.D., et al., "Vasoactive Intestinal Peptide–Receptor . . . Endocrine Tumors," The New England Journal of Medicine, vol. 331, No. 17, pp.1116–1121, Oct. 27, 1994.
K. Frank–Raue, et al., "Somatostatin Receptor Imaging in Persistent Medullary Thyroid Carcinoma," Clinical Endocrinology (1995) 42, pp. 31–37.
Gabor Halmos, et al., "Characterization of Bombesin/Gastrin–Releasing Peptide . . . Gastric Cancer" Cancer Letters 85 (1994), pp.111–118.
Antal Orosz, et al., "New Short–Chain Analogs of Substance–P . . . Cells in vitro and in vivo," Int. J. Cancer, 60, pp.82–87, (1995).
Karoly Szepeshazi, et al., "Combination of Nitrosamine–Induced . . . Bombesin/GRP Antagonist," Int'l. Journal of Pancreatology, vol. 16, Nos. 2–3, pp.141–149, Oct.–Dec. 1994.
P. Heinz–Erian, et al., "Characterization of a New Group of Substituted Substance P . . . Antagonists," Abstracts of Papers, pp.1455, May 1986.
Tim Mosmann, "Rapid Colorimetric Assay For Cellular Growth and . . . Cytotoxicity Assays," Journal of Immunological Methods, 65, (1983), pp.55–63.
I. Zachary, et al., "Bombesin, Vasopressin, and Endothelin Rapidly Stimulate . . . 3T3 Cells," Proc. Natl. Acad. Sci. USA, vol. 88, pp.4577–4581, Jun. 1991.
I. Gozes, et al., "Vasoactive Intestinal Peptide Potentiates Sexual Behavior . . . Antagonist," Endocrinology, vol. 125, No. 6, pp.2945–2949, 1989.
P. Woll, et al., "[D–ARG$^1$,D–PHE$^5$,D–TRP$^{7,9}$, LEU$^{11}$] Substance P, A Potent Bombesin . . . in vitro," Proc. Natl. Acad. Sci. USA, vol. 85, pp.1859–1863, Mar. 1988.

(List continued on next page.)

*Primary Examiner*—Cecilia J. Tsang
*Assistant Examiner*—C. Delacroix-Muirheid
*Attorney, Agent, or Firm*—Ladas & Parry

[57] ABSTRACT

The present invention provides a novel method for the establishment of tumorigenic cell lines from biopsies of human or animal tumors. The method includes preparing a single-cell suspension of a tumor cells by injecting cell culture medium into an isolated tumor or a portion thereof to flush out the tumor cells. The tumor or portion thereof may be in a cell culture maintenance medium. The step of injecting cell culture medium into the isolated tumor or portion thereof involves piercing the tumor or portion thereof with a needle to inject the cell culture medium and flush out the tumor cells. The steps of piercing the tumor or portion thereof with a needle and injecting the cell culture medium to flush out the tumor cells preferably are repeated until the single-cell suspension has a particular cell density. The method also includes establishing a primary tumor cell culture by growing the cells from the single-cell suspension in a cell culture medium.

19 Claims, 1 Drawing Sheet

OTHER PUBLICATIONS

M. Jaggi, et al., "New Sensitive and Specific Elisa For Detection . . . Supernatants," Journal of Immunoassay, 15(2), pp. 129–146 (1994).

K. Gulya, et al., "Cyclic Somatostatin Octapeptide Analogues With High . . . Opioid Receptors," Life Sciences, vol. 38, No. 24, pp.2221–2229, 1986.

M. Brown, et al., "Somatostatin: Analogs With Selected Biological Activities," Science, vol. 196, pp.1467–1469, (1977).

J. T. Pelton, et al., "Design and Synthesis of Conformationally Constrained Somatostatin . . . Receptors," J. Med. Chem. 1986, 29, pp.2370–2375.

M. Jaggi, et al., "Establishment of Tumorigenic Cell Lines From Biopsies . . . Adenocarcinomas," Journal of Basic & Applied Biomedicine (1995) 3 (4), pp. 27–35.

METHOD FOR ESTABLISHING A TUMOR-CELL LINE BY PREPARING SINGLE-CELL SUSPENSION OF TUMOR CELLS FROM TUMOR BIOPSIES

This application is a continuation-in-part of application Ser. No. 08/727,679 filed on Oct. 8, 1996.

FIELD OF INVENTION

The present invention relates to a technique to culture in vitro primary tumor samples. This technique is different from the standard protocol in that it obviates the laborious procedure of chopping and mincing the tumor tissue and treating it with enzymes. In the present invention, the cells are flushed out of the tumor tissue and allowed to grow in vitro, as a single-cell suspension. The tumor cell lines resulting from the method of the present invention are superior to the tumor cell lines resulting from the standard protocol in that they are more tumorigenic. Using the method of the invention, new potential anticancer drugs for the treatment of cancers such as adenocarcinomas (more specifically, adenocarcinoma of the colon, lung, breast, prostate, ovary, pancreas, duodenum, intestines, kidney and liver) or for treatment of cancers characterized by loosely bound tumor cells can be tested more efficiently.

The in vitro and in vivo models described herein are of great value in identifying novel anticancer agents and developing new treatment strategies for cancer. Establishment of primary tumor cell cultures facilitates identification and characterization of the key growth factors responsible for uncontrolled growth and, thereby, facilitates designing cancer cell targeted therapy. The primary tumor cell cultures are established by optimizing the procedure for isolation of cells and culture conditions to achieve continuous growth of the primary tumor cells that represent most of the subpopulation of cells present in the tumor in situ. Transfer of primary tumor cells to laboratory animals further aids in testing new anticancer agents.

BACKGROUND

Reports in the scientific literature disclose that primary tumor cultures have been established by chopping and mincing the tumor tissue and treating it with various enzymes to finally grow it as an explant (Peters, et al., "Preparation of Immunotherapeutic Autologous Tumor Cell Vaccines from Solid Tumors," *Cancer Research* 39 (1979) :1353–60). This method of enzymatic digestion is not very efficient and is prone to contamination (Vose, "Separation of Tumor and Host Cell Populations from Human Neoplasm," in *Cancer Cell Organelles*, eds. E. Reid, G. M. W. Cook, and D. Y. Morre (Chichester, United Kingdom: Horwood, Ltd., Publishers, (1981):45–56).

Colon cancer tumor induction in nude mice has been previously reported with a success rate of 60–80% (Giovanella, et al., "Correlation Between Response to Chemotherapy of Human Tumors in Patients and in Nude Mice," *Cancer* 52 (1983):1146–52). The method described in the Giovanella article involved the xenografting of primary human tumor tissue in nude mice followed by transfer of the cells from the tumor to a culture after the tumor tissue had been passaged 2–3 times in the mice. Various routes have been used for induction of tumors in nude mice with varying success rates (Giavazzi, et al., "Metastatic Behaviour of Tumor Cells Isolated from Primary and Metastatic Human Colorectal Carcinomas Implanted into Different Sites in Nude Mice," *Cancer Research* 46 (1986):1928–33). The orthotopic transplantation of histologically intact tissue of human pancreatic cancer and human metastatic colon cancer in nude mice has also been reported (Fu, et al., "A Metastatic Nude-Mouse Model of Human Pancreatic Cancer Constructed Orthotopically with Histologically Intact Patient Specimens," *Proc. Natl. Acad. Sci. U.S.A.* 89 (1992) :5645–49; Fu, et al., "Models of Human Metastatic Colon Cancer in Nude Mice Orthotopically Constructed by Using Histologically Intact Patient Specimens," *Proc. Natl. Acad. Sci. U.S.A.* 88 (1991):9345–49). The following table A lists in vitro and in vivo models for different cancer types.

TABLE A

| Tumor Type | Model | Reference |
| --- | --- | --- |
| Pancreatic cancer | In vivo | Fu, et al., "A Metastatic Nude-Mouse Model of Human Pancreatic Cancer Constructed Orthotopically with Histologically Intact Patient Specimens," Proc. Natl. Acad. Sci. USA 89 (1992): 5645–49. |
| Colorectal cancer | In vivo and in vivo | Giavazzi, et al., "Metastatic Behaviour of Tumor Cells Isolated from Primary and Metastatic Human Colorectal Carcinomas Implanted into Different Sites in Nude Mice," Cancer Research 46 (1986): 1928–33. |
| Colon cancer | In vivo | Fu, et al., "Models of Human Metastatic Colon Cancer in Nude Mice Orthotopically Constructed by Using Histologically Intact Patient Specimens," Proc. Natl. Acad. Sci. USA 88 (1991): 9345–49. |
| Breast cancer | In vitro and in vivo | Rae-Venter, et al., "Growth of Human Breast Carcinomas in Nude Mice and Subsequent Establishment in Tissue Culture," Cancer Research 40 (1980): 95–100. |
| Melanoma, colorectal cancer, breast carcinoma | In vivo | Giovanella, et al., "Correlation Between Response to Chemotherapy of Human Tumors in Patients and in Nude Mice," Cancer 52 (1983): 1146–52. |

SUMMARY

The invention includes a method of preparing a single-cell suspension of tumor cells by injection of cell culture medium into an isolated tumor or a portion thereof to flush out the tumor cells. The tumor or portion thereof may be maintained in a cell culture medium. The step of injecting cell culture medium into the isolated tumor or portion thereof involves piercing the tumor or portion thereof with a needle to inject the cell culture medium and flush out the tumor cells. The term "flush out" incorporates the event of the fluid coming out of the tumor or portion thereof after injection into the tumor or portion thereof of cell culture medium, wherein the fluid coming out of the tumor or portion thereof contains the cells released from the tumor. The steps of piercing the tumor or portion thereof with a needle and injecting the cell culture medium to flush out the tumor cells preferably are repeated until a single-cell suspension is obtained having a particular cell density.

The invention also includes a method of establishing a primary tumor cell culture, the method including the steps of: (a) preparing a single-cell suspension according to the method described in the previous paragraph; and (b) growing the cells from the single-cell suspension in a cell culture medium. The cells grown in step (b) may be passaged.

DETAILED DESCRIPTION

Figure 1:
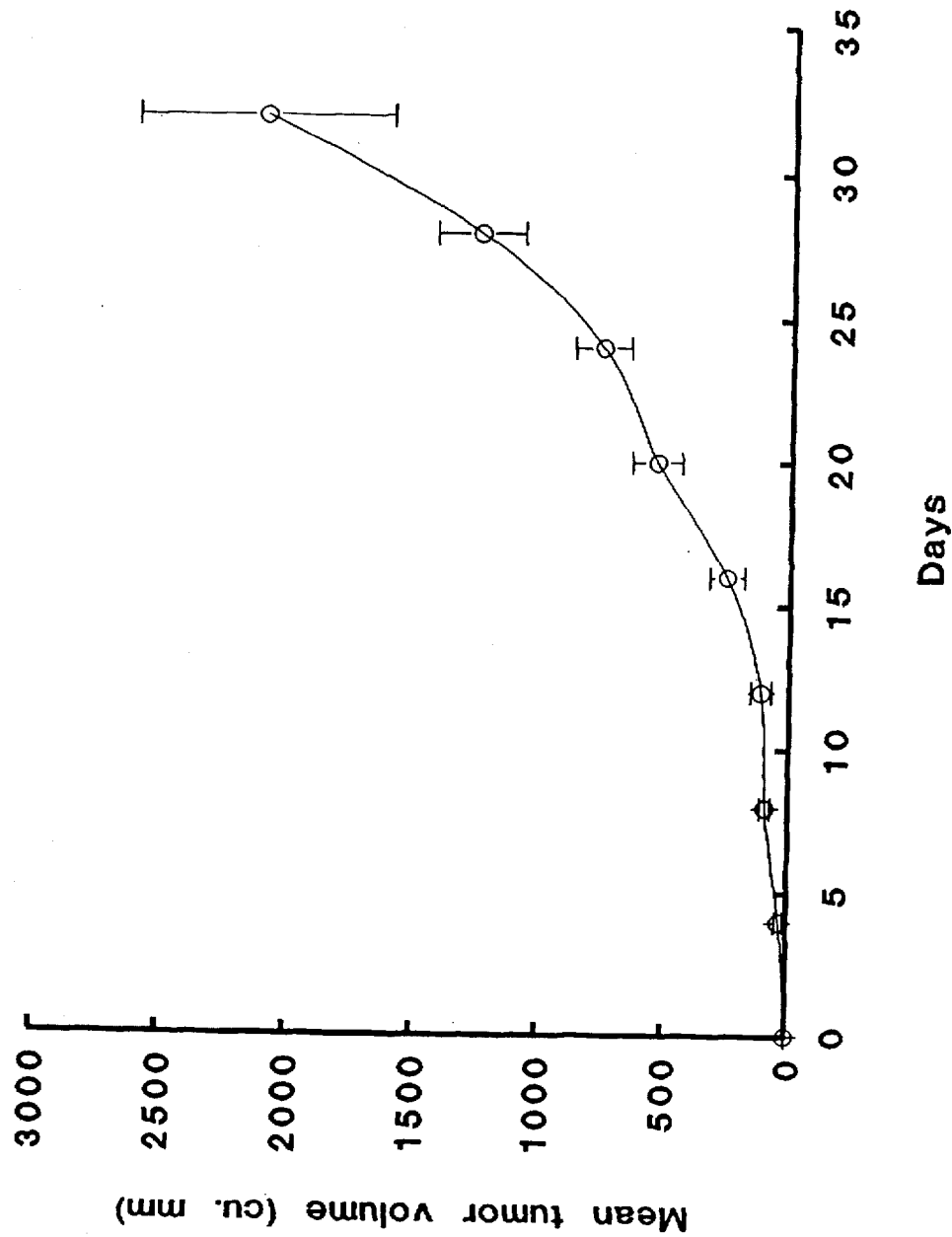
FIG. 1 shows the mean tumor volumes PCTHCA injected subcutaneously in nude mice from day 4 to 32.

According to this invention, a tumor sample is obtained. The tumor sample is preferably obtained directly from a patient or an animal, although the tumor sample obtained from a patient or an animal can be stored for up to approximately six months before use. It is preferred that the sample be stored for less than six months before use. Before use, the fatty tissue and necrotic tissue from the tumor sample are removed. The remaining tissue is incubated in a cell culture medium, and then the tissue is cut into small pieces (e.g., ranging in size from about 1×1×1 mm to about 10×10×10 mm and preferably about 5×5×5 mm in size). Cell culture medium that can be used comprises RPMI, fetal calf serum, gentamycin, and streptomycin. Nystatin may also be added to the cell culture medium. Other culture medium such as DMEM (Dulbeccos Modified Essential Medium), F12 Medium, Hanks Balanced Salt Solution, HAM Medium, buffered saline or any other suitable cell culture medium may be used. The tumor cells are then released and dispersed from the tumor tissue by piercing it with a needle and injecting cell culture medium into the tumor. It is preferred that the tumor is injected by filing a 5 ml or 10 ml syringe with approximately 5 ml of cell culture medium and piercing the tumor tissue about halfway through using a needle preferably a 21 gauge needle ½ inch or 1 inch in length and injecting medium into the tissue slowly. The fluid coming out of the tumor contains the cells released from the tumor. This process results in the dislodgment of cells from the tumor tissue which come out with the cell culture medium. The tumor cells are slowly flushed out of the tissue, and a single cell suspension is obtained. This procedure may be repeated several times until a cell density of at least approximately $10^3$ cells/ml is obtained. The viability of the tumor cells in the single cell suspension may be checked by trypan blue.

To establish a primary tumor cell culture, cells in the single cell suspension are plated in culture dishes containing cell culture medium. The cultures are maintained in an incubator, wherein the concentration of $CO_2$ and $O_2$ may be kept constant. The cell debris present in the cultures should be gently removed as necessary, and fresh cell culture medium should be added regularly. Small colonies will start to form; and these colonies subsequently will increase in size to merge with each other. When confluence of the colonies is attained, the cells may be subcultured.

The cells are subcultured by incubating them with trypsin (e.g., 0.25% trypsin in the cell medium) in the incubator for a period of time ranging from approximately 5 minutes to approximately 15 minutes (preferably approximately 10 minutes). The effect of trypsin is arrested by adding fresh fetal calf serum (e.g., 10%). Then the cells are scraped off the culture surface and transferred to a plate with multiple wells. Approximately 1000 to 100,000 cells are added to each well. After a period of time ranging from approximately 5 days to approximately 10 days (preferably 7 days), the cultured cells are transferred from the plate to a medium-sized flask and then to a large-sized flask. The expanded culture, which is maintained in the large-size flask, constitutes the "first passage." Approximately every 10 days, the cells may be passaged again. The true identity of the passaged cells may be routinely monitored by indirect immunofluorescence using as a probe a tumor specific monoclonal antibody.

The ability of the primary tumor cell culture to form colonies in soft agar is a characteristic feature of transformed cells; and, therefore, the presence of tumor cells may be checked by growing the cells in soft agar in the conventional way. The following protocol, for example, may be used. The soft agar is prepared by conventional methods. For instance, an approximately 1% solution of tissue culture grade agarose may be prepared by melting it at approximately 90° C. for approximately two hours and subsequently sterilizing it by gamma irradiation. Healthy primary tumor cells are counted and suspended in double strength RPMI 1640 medium such that 2 ml contains approximately 50 to 200 cells, preferably 100 cells. The concentration of fetal calf serum (FCS) in the medium is kept at approximately 20%. 2 ml of this cell suspension was plated in each well of a multiple-well culture plate and then an approximately equal volume of 1% agar solution was added to each well. The final concentration of solidified agar is approximately 0.5%, the final concentration of fetal calf serum is approximately 10%, and the final concentration of RPMI 1640 is approximately normal strength. The cultures then are incubated at approximately 37° C. in a 5% $CO_2$ incubator. The cultures are fed with regular cell culture medium at intervals of approximately three to four days to prevent the agar from drying out. If the primary tumor cells have the ability to form colonies in soft agar, small colonies will become visible and slowly will increase in size; and if left, eventually the colonies will start merging with each other.

Although a few exemplary embodiments of this invention are described in detail in the following sections, those skilled in the art will readily appreciate that many modifications are possible in the exemplary embodiments without materially departing from the novel teachings and advantages of this invention. Accordingly, all such modifications are intended to be included within the scope of this invention.

In Vitro Studies

Tumor tissue biopsies were collected from 12 patients who were diagnosed with colon cancer on the basis of clinical history, fine needle aspiration cytology (FNAC), and histopathology. Out of the twelve patients, seven were males and five females. Their ages were in the range of 47 to 74 years. Five out of twelve patients had cancer of the ascending colon; five had cancer of the descending colon; and two had cancer of the transverse colon.

For each patient, a tumor biopsy was taken from the periphery of the tumor that contained roughly the highest proportion of tumor cells and that was not in direct contact with fecal matter. The biopsy was collected in a cell culture medium comprising RPMI 1640 (Biological Industries, Israel), 5% fetal calf serum (Biological Industries, Israel), gentamycin (100 ug/ml, Fulford), and streptomycin (650 µg/ml, Sarabhai Chemicals, India). The biopsy tissue was transported from the operation theater to the culture room at approximately 4° C. Cultures were initiated within approximately 4 to 12 hours of biopsy collection.

The tumor biopsy was transferred to a cell culture medium comprising RPMI 1640 (Biological Industries, Israel), 5% fetal calf serum (Biological Industries, Israel), gentamycin (100 ug/ml, Fulford), streptomycin (650 µg/ml, Sarabhai Chemicals, India) and nystatin (0.1 µg/ml) in an aseptic laminar hood. The fatty tissue and the necrotic tissue were removed. The remaining tissue was then incubated in the cell culture medium for at least ten minutes and for not more than 40 minutes. It is preferred that the tissue is incubated for approximately 30 minutes. After the tissue is incubated it is then transferred to fresh cell culture medium comprising RPMI 1640 (Biological Industries, Israel), 5% fetal calf serum (Biological Industries, Israel), gentamycin (100 µg/ml, Fulford), streptomycin (650 µg/ml, Sarabhai Chemicals, India) and nystatin (0.1 µg/ml). After four to five such serial transfers, the tissue was used for the preparation of a single cell suspension. The tissue was cut into small pieces of about 5×5×5 mm in size. Additional serial transfers can take place before the tissue is cut into small pieces. The cells were then released and dispersed from the tumor tissue by piercing the tumor tissue with a 21-gauge needle preferably ½ inch or 1 inch in length and injecting cell culture medium comprising RPMI 1640, 10% fetal calf serum (FCS), gentamycin (50 µg/ml,) and streptomycin (325 µg/ml) into the tissue. The cells were slowly flushed out of the tissue and a single cell suspension was obtained. This procedure was repeated several times until a cell density of at least approximately $10^3$ cells/ml was obtained. The fluid coming out of the tumor contains the cells released from the tumor. (The remaining tissue was cut into small pieces and stored at $-70°$ C. in neat FCS containing 10% dimethyl sulfoxide. Tumor tissue stored in this way can be used for establishment of in vitro cultures even after 6 months although it is preferred that the tissue be used before 6 months.) Before the tumor cells were plated, the cell viability of the single cell suspension was checked by trypan blue and was found to be between approximately 80–90%.

Approximately $10^3$ cells/ml were plated on day 0 in 55 mm petri dishes containing the cell culture medium that was injected into the tumor tissue. The cultures were maintained at approximately $37°$ C. in a $CO_2$ incubator, with the concentration of $CO_2$ kept constant at approximately 5% and the concentration of $O_{20}$ kept constant at approximately 95%. The cell debris present in the cultures was gently removed by conventional methods, and fresh cell culture medium was added to the cultures every third day. Cell growth was observed within approximately 24–48 hours of plating, and the cells started adhering to the culture surface. It was observed that approximately 95% of the cells had a round morphology, a translucent cytoplasm, and a large nucleus containing single nucleolus. These observations were consistent with the histology of primary tumor cells of human colon adenocarcinoma. By approximately days 5–7, small colonies started forming; and these colonies subsequently increased in size to merge with each other by approximately day 9. Confluence was attained by approximately day 10, when the cells were subcultured.

On day 10 when the cells were subcultured, the cells were incubated at approximately $37°$ C. with 0.25% trypsin for 10 minutes in a $CO_2$ incubator. This incubation step can take place on any of days 5, 6, 7, 8, 9, 10, 11, 12, 13, 14, or 15. The effect of trypsin was arrested by adding fresh 10% FCS. The cells were scraped off the culture surface, counted, and expanded by transferring them to 6-well plates. After one week, the cultured cells were transferred from 6-well plates to 25 $mm^3$ flasks and then the cells from the multiple 25 $mm^3$ flasks were combined into a 75 $mm^3$ flask. The expanded culture, which was maintained for 4 to 10 days in the 75 $mm^3$ flask, was designated "first passage". These were then passaged every 10 days and the medium was changed between day 3 and 6. The cell culture medium that was used comprised RPMI 1640, 5% fetal calf serum, gentamycin (100 ug/ml), streptomycin (650 µg/ml) and nystatin (0.1 µg/ml). Six out of the twelve primary tumor tissues that were established as cultures were passaged in vitro 38 times, four of them were passaged 12 times, and the remaining two of them were passaged six times each. In all passages the cell culture medium is changed every 3 to 6 days.

The identity of the passaged cells was routinely monitored by indirect immunofluorescence using as a probe an adenocarcinoma specific monoclonal antibody that recognizes a 90 kD glycoprotein on the membrane. Approximately 90% of the tumor cells stained with the adenocarcinoma specific marker as revealed by bright fluorescence on the periphery of the tumor cells, when viewed under the UV light. Thus, the reactivity of the cultured cells to the monoclonal antibody when checked at different passages of the culture was found to be adenocarcinoma positive.

The identity of the cells as tumor cells was also checked by growing the cells which had been passaged at least 5 times in vitro in soft agar. An approximately 1% solution of tissue culture grade agarose was prepared by melting it at approximately $90°$ C. for approximately two hours and subsequently sterilizing it by gamma irradiation. Healthy primary tumor cells were counted and suspended in double strength RPMI L1640 medium such that 2 ml contained approximately 100 cells. The concentration of fetal calf serum in the medium was kept at approximately 20%. 2 ml of this cell suspension was added to each well in a six-well culture plate. The cell suspension was plated and an approximately equal volume of 1% agar solution was added to the plated cell suspension. The final concentration of solidified agar was approximately 0.5%, fetal calf serum was approximately 10%, and RPMI 1640 was approximately normal strength. The cultures then were incubated at approximately $37°$ C. in a 5% $CO_2$ incubator. The cultures were fed with regular cell culture medium at intervals of approximately three to four days. Small colonies of cells became visible after approximately 5–7 days. Approximately 0.5 ml of the cell culture medium was added on top of the agar to prevent the drying up of the agar. When the colonies became visible, the cells had a round, translucent morphology. The colonies slowly increased in size, and by day 30 they started merging with each other. The primary tumor cells of human colon adenocarcinoma when cultured in vitro in agar did not show contact inhibition.

The methods described above were used for developing cultures of primary tumor cells of human colon adenocarcinoma in vitro and for monitoring the cells' viability, true identity, growth, and tumorigenicity. A success rate of 100% ($^{12}/_{12}$) was achieved in establishing the primary tumor cell cultures. A success rate of 100% was considered achieved when all twelve cell lines established were passaged at least 5 times in vitro.

In Vivo Studies

The primary tumor cells of human colon adenocarcinoma that were cultured in vitro and identified as adenocarcinoma cells by the monoclonal antibody probe were used for tumor induction in nude mice. Six-to-eight-week-old nude mice of NIH strain (nu/nu) of both sexes were selected for tumor induction and were maintained in a sterile environment. Three mice per cell line were used. All the animals selected were in good health as indicated by their stable weight and normal activity. All the animals were maintained on a daily cycle of 12 hours light and 12 hours dark. The animals were fed with an autoclaved standard pellet diet and water ad libitum. Sterilized cages were changed weekly. For standardization of the technique, various sites of injection and tumor cell concentrations optimum for tumor formation were tried. Tumor cell concentrations ranging from $10^6$ cells/0.2 ml to $2×10^7$ cells /0.5 ml were injected in the nude mice. The cells came from a 4-to-5-day-old culture from an established cell line that had undergone at least 5 passages. Injection sites were selected from the peritoneum, subcutaneously on the back of the animal, and subcutaneously on the abdomen. Each mouse was injected in one of these three sites. It was found that injection subcutaneously on the abdomen was optimum. The growth kinetics of the abdominal tumors were monitored by measuring the dimensions of the tumor using a vernier calliper, from which the volume was mathematically derived (Winn, 1959). The abdominal tumor was photographed every third day, and the weight was determined after excision of the tumor.

It was found that a primary tumor cell concentration of $10^7$ cells/0.3 ml of the tumor cell suspension of primary tumor cells of human colon adenocarcinoma was optimum. Cell numbers less than approximately $10^7$ did not result in tumor formation. Similarly, cells injected into the back or the peritoneum of the animal did not result in the formation of a visible tumor mass.

In another experiment, a primary tumor cell concentration of $10^7$ cells/0.3 ml of the tumor cell suspension was injected subcutaneously on the abdomen in 24 nude mice. A palpable mass at the site of the tumor cell injection appeared within 3 to 4 days post-injection (day 0 is the day when the mice were injected with the cells), and the mass subsequently began to grow as a solid tumor. The mean tumor volume was about 100 mm$^3$ by day 12 and increased to approximately 300 mm$^3$ by day 16. A phase of rapid growth was observed from day 16 to 28, at which time the volume increased to about 1500 mm$^3$. From day 28 to 32, there was a very rapid growth of the tumor and a volume of approximately 2400 mm$^3$ was attained. The tumor volume rarely increased beyond 3000 mm$^3$. A necrotic spot appeared in all of the tumors in all of the mice. The necrotic spot was about 1 mm diameter and appeared in the center of the tumor after about days 14–16, and the spot increased in size with time. FIG. 1 shows the mean tumor volumes.

All of the mice died between day 28 and day 32.

Additional In Vitro and In Vivo Studies

Cells from the tumor tissue growing in the nude mice then were cultured in vitro. For this, a tumor-bearing mouse was sacrificed on day 25. The tumor was excised; and a single-cell suspension of tumor cells from the tumor was prepared in a manner identical to the one described earlier for human primary tumors. Cultures of primary tumor cells of human colon adenocarcinoma were reestablished from the excised tumor of the nude mouse. The cultured cells retained adenocarcinoma characteristics as revealed by testing with the monoclonal antibody probe. The cells could be passaged several times in vitro. The cultured tumor cells also retained their ability to form colonies in soft agar, thus indicating that the cells retained their tumorigenic properties. The cultured tumor cells were reinjected into nude mice to check the tumor growth in vivo. A cell suspension having a concentration of $10^7$ cells/0.3 ml was prepared and injected subcutaneously on the abdomen of the nude mouse. The tumor growth kinetics were similar to the growth kinetics obtained when established cell line from primary tissue was injected at same concentration and route.

This specification incorporates herein the following article by this reference: Jaggi, M., Mukherjee, R., "Establishment of Tumorigenic Cell Lines from Biopsies of Human Colon Adenocarcinomas," *Journal of Basic & Applied Biomedicine*, 3(4):27–35 (1995).

The invention illustratively disclosed herein suitably may be practiced in the absence of any element which is not specifically disclosed herein. Thus, the invention may comprise, consist of, or consist essentially of the elements disclosed herein.

Although the present invention has been described in considerable detail with reference to certain preferred embodiments, the spirit and the scope of the appended claims should not be limited to the description of the preferred embodiments contained herein. Thus, although a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the followings claims.

The following claims are entitled to the broadest possible scope consistent with this application.

We claim:

1. A method of preparing a single-cell suspension of tumor cells, the method comprising injecting cell culture medium into an isolated tumor or a portion thereof to flush out the tumor cells.

2. A method as claimed in claim 1, wherein the step of injecting cell culture medium into the isolated tumor or portion thereof comprises piercing the tumor or portion thereof with a needle to inject the cell culture medium and flush out the tumor cells.

3. A method as claimed in claim 1, wherein the tumor or portion thereof is in a cell culture medium.

4. A method as claimed in claim 2, wherein the tumor or portion thereof is in a cell culture medium.

5. A method as claimed in claim 2, wherein the steps of piercing the tumor or portion thereof with a needle and injecting the cell culture medium to flush out the tumor cells are repeated until the single-cell suspension has a cell density of about $10^3$ cells/ml to about $10^6$ cells/ml of suspension.

6. A method as claimed in claim 4, wherein the steps of piercing the tumor or portion thereof with a needle and injecting the cell culture medium to flush out the tumor cells are repeated until the single-cell suspension has a cell density of approximately $10^3$ cells/ml of suspension.

7. A method of establishing a primary tumor cell culture, the method comprising the steps of:
   (a) preparing a single-cell suspension according to the method claimed in claim 1; and
   (b) growing the cells from the single-cell suspension in a cell culture medium.

8. A method of establishing a primary tumor cell culture as claimed in claim 7, wherein growing the cells in step (b) further comprises passaging the cells at least four times.

9. A method of establishing a primary tumor cell culture, the method comprising the steps of:
   (a) preparing a single-cell suspension according to the method claimed in claim 2; and
   (b) growing the cells from the single-cell suspension in a cell culture medium.

10. A method of establishing a primary tumor cell culture as claimed in claim 9, wherein growing the cells in step (b) further comprises passaging the cells.

11. A method of establishing a primary tumor cell culture, the method comprising the steps of:
   (a) preparing a single-cell suspension according to the method claimed in claim 3; and
   (b) growing the cells from the single-cell suspension in a cell culture medium.

12. A method of establishing a primary tumor cell culture as claimed in claim 11, wherein growing the cells in step (b) further comprises passaging the cells.

13. A method of establishing a primary tumor cell culture, the method comprising the steps of:

(a) preparing a single-cell suspension according to the method claimed in claim 4; and (b) growing the cells from the single-cell suspension in a cell culture medium.

14. A method of establishing a primary tumor cell culture as claimed in claim 13, wherein growing the cells in step (b) further comprises passaging the cells.

15. A method of establishing a primary tumor cell culture, the method comprising the steps of:

(a) preparing a single-cell suspension according to the method claimed in claim 5; and (b) growing the cells from the single-cell suspension in a cell culture medium.

16. A method of establishing a primary tumor cell culture as claimed in claim 15, wherein growing the cells in step (b) further comprises passaging the cells.

17. A method of establishing a primary tumor cell culture, the method comprising the steps of:

(a) preparing a single-cell suspension according to the method claimed in claim 6; and (b) growing the cells from the single-cell suspension in a cell culture medium.

18. A method of establishing a primary tumor cell culture as claimed in claim 17, wherein growing the cells in step (b) further comprises passaging the cells.

19. A method of preparing a single cell suspension of tumor cells, the method comprising the steps of:

(a) transferring isolated tumor tissue to a cell culture medium;

(b) incubating for 10 to 40 minutes;

(c) transferring the tumor tissue to fresh cell culture medium;

(d) repeating step c) four to five times;

(e) cutting the tumor tissue into small pieces;

(f) injecting into the tumor tissue cell culture medium; and (g) flushing cells out of the tumor tissue until a single cell suspension is obtained.

* * * * *